United States Patent [19]

Gaddy

[11] Patent Number: 5,593,886
[45] Date of Patent: Jan. 14, 1997

[54] CLOSTRIDIUM STAIN WHICH PRODUCES ACETIC ACID FROM WASTE GASES

[76] Inventor: James L. Gaddy, 2207 Tall Oaks Dr., Fayetteville, Ark. 72703

[21] Appl. No.: 258,446

[22] Filed: Jun. 10, 1994

Related U.S. Application Data

[62] Division of Ser. No. 968,857, Oct. 30, 1992, abandoned.

[51] Int. Cl.⁶ .................................................... C12N 1/20
[52] U.S. Cl. ........................ 435/252.7; 435/163; 435/140
[58] Field of Search ................................ 435/252.7, 163, 435/140

[56] References Cited

U.S. PATENT DOCUMENTS

| | | | |
|---|---|---|---|
| 4,568,644 | 2/1986 | Wang et al. | 435/161 |
| 4,652,526 | 3/1987 | Hsu | 435/253 |
| 4,771,001 | 9/1988 | Bailey et al. | 435/139 |
| 4,921,799 | 5/1990 | Kitaura et al. | 435/167 |
| 4,935,360 | 6/1990 | Klemps et al. | 435/140 |
| 5,036,005 | 7/1991 | Tedder | 435/161 |
| 5,059,288 | 10/1991 | Curry | 203/43 |
| 5,077,208 | 12/1991 | Sublette | 435/168 |
| 5,173,429 | 12/1992 | Gaddy | 435/163 |

FOREIGN PATENT DOCUMENTS

| | | | |
|---|---|---|---|
| 0282750 | 9/1988 | European Pat. Off. | 435/266 |

OTHER PUBLICATIONS

Biotechnology Company Set For Fayetteville, Patricia May, Springdale Morning News, Oct. 29, 1992, p. 1A.
Industrial Innovations For Tomorrow, New Process Uses Bacteria To Transform Waste Gases Into Useful Chemicals, U.S. Dept. of Energy Publication Aug. 1992.
The Production of Acetic Acid From Carbon Dioxide and Hydrogen by An Anaerobic Bacterium, Tsuyoshi Morinaga and Naoki Kawada, Journal of Biotechnology, 14 (1990), 187–194.
Isolation From Soil and Properties of the Extreme Thermophile Clostridium Thermohydrosulfuricum, Jurgen Wiegel et al., Journal of Bacteriology, Sept. 1979, pp. 800–810.
Solvent Equilbria for Extraction of Carboxylic Acids From Water, James M. Wardell and C. Judson King, Journal of Chemical and Engineering Data, vol. 23, No. 2, 1978, pp. 144–148.
Removing Carboxylic Acids From Aqueous Wastes, CEP, May 1977 R. W. Helsel, Hydroscience Environmental Systems, Knoxville, TN.
Acetogenium Kivui, A New Thermophilic Hydrogen–Oxidizing, Acetogenic Bacterium, J. A. Leigh et al., Arch Microbiol. 129:275–2.
Sporomusa, A New Genus of Gram–Negative Anaerobic Bacteria Including Sporomusa Sphaeroides Spec. Nov. and Sporomusa Ovata Spec. Nov., Moller et al., Arch Microbiology (1984) 139:388–3.
Acetobacterium, A New Genus of Hydrogen–Oxidizing, Carbon Dioxide–Reducing Anaerobic Bacteria, Balch et al., International Journal of Systematic Bacteriology, Oct. 1977, pp. 355–361.

Peptostreptococcus Productus Strain That Grows Rapidly With Co as the Energy Source, William H. Lorowitz and Marvin P. Bryan Applied and Environmental Microbiology, May 1984, pp. 70–74.
Growth of Eubacterium Limosum With Carbon Monoxide as the Energy Source, B. R. Sharak Genthner ∂M. P. Bryant. Applied and Environmental Microbiology, Jan. 1982, pp. 70–74.
Carbon Monoxide Metabolism of the Methylotrophic Acidogen Butyribacterium Methylotrophicum, Lee Lynd R. Kerby and J. G. Zeikus, Journal of Bacteriology, Jan. 1982, pp. 255–263.
Revival of the Name Clostridium Aceticum, Gerhard Gottschalk and Manfred Braun, International Journal of Systematic Bacteriology, Oct. 1981, p. 476.
Hydrogen Utilization by Clostridia in Sewage Sludge, Kyoko Ohwaki and R. F. Hungate, Applied and Environmental Microbiology, Jun. 1977, pp. 1270–1274.
Single–Carbon Catabolism in Acetogens: Analysis of Carbon Flow in Acetobacterium Woodii and Butyribacterium Methylotrophicum by Fermentation and $^{13}C$ Nuclear Magnetic Resonance Measurement, R. Kerby, et al., Journal of Bacteriology, Sep. 1983, pp. 1208–1218.
Production of Acetic Acid by Clostridium Thermoaceticum in Batch and Continuous Fermentations, K. Sugaya, et al., Biotechnology and Bioengineering, vol. XXVIII, (1986), pp. 678–683.
Isolation of a Strain of Clostridium Thermoaceticum Capable of Growth and Acetic Acid Production at ph 4.5, Robert D. Schwartz and Frederick A. Keller, Jr., Applied and Environmental Microbiology Jan. 1982, pp. 117–123.
Acetic Acid Production by Clostidium Thermoaceticum in ph Controled Batch Fermentations at Acidic ph Robert D. Schwartz and Fredrick A. Keller Jr., Applied and Environmental Microbiology, Jun. 1982, pp. 1385–1392.
Characterization of the $H_2$ and Co–Dependent Chemolithutropic Potentials of the Acetogens Clostridium Thermoaceticum and Acetogenium Kivui, Steven L. Daniel, et al., Journal of Bacteriology, Aug. 1990, pp. 4464–4471.

(List continued on next page.)

Primary Examiner—Irene Marx
Attorney, Agent, or Firm—Daniel R. Alexander; Head, Johnson & Kachigian

[57] ABSTRACT

A method and apparatus for converting waste gases from industrial processes such as oil refining, carbon black, coke, ammonia, and methanol production, into useful products. The method includes introducing the waste gases into a bioreactor where they are fermented to various organic acids or alcohols by anaerobic bacteria within the bioreactor. These valuable end products are then recovered, separated and purified. In an exemplary recovery process, the bioreactor raffinate is passed through an extraction chamber into which one or more non-inhibitory solvents are simultaneously introduced to extract the product. Then, the product is separated from the solvent by distillation. Gas conversion rates can be maximized by use of centrifuges, hollow fiber membranes, or other means of ultrafiltration to return entrained anaerobic bacteria from the bioreactor raffinate to the bioreactor itself, thus insuring the highest possible cell concentration.

7 Claims, 4 Drawing Sheets

OTHER PUBLICATIONS

Clostridium Thermosaccharolyticum Strain Deficient in Acetate Production, David M. Rothstein, Journal of Bacteriology, Jan. 1986, pp. 319–320.

Nickel Transport by the Thermophilic Acetogen Acetogenium Kivui Applied and Environmental Microbiology, May 1989, pp. 1078–1081.

Differential Effects of Sodium on Hydrogen–and Glucose–Dependent Growth of the Acetogenic Bacterium Acetogenium KIV Hsuichin Yang and Harold L. Drake, Applied and Environmental Microbiology, Jan. 1990, pp. 81–86.

Influence of Environmental Factors in the Production of R(–)–1,2–Propanediol by Clostridium Thermosaccharolyticum, F. Sanchez–Riera, et al., Biotecnology Letters, vol. 9, No. 7, 449–4.

The Active Species of '$CO_2$' Utilized by Reduced Ferredoxin: $CO_2$Oxidoreductase from Clostridium Pasteurianum, R. K. Thauer, et al., European Journal of Biochemistry, 55, 111–117 (1975).

Biological Production of Alcohols from Coal Through Indirect Liquefaction, S. Barik, et al., The Humana Press, 1988, pp. 363–378.

Biological Production of Liquid and Gaseous Fuels From Synthesis Gas, K. T. Klasson et al., Applied Biochemistry and Biotechnology, vol. 24/25, 1990.

The Biological Production of Ethanol from Synthesis Gas, J. L. Vega et al., Applied Biochemistry and Biotechnology, vol. 20/21, 1988.

Parameters Affecting the Kinetics of Ethanol Production From CO3 $co_2$ and $H_2$by Clostridium Ljungdahlii, K. M. O. Lundback, et al Presented at Twelfth Symposium on Biotechnology for Fuels and Chemicals, Gatlinburg, Tennessee, May 1990.

Clostridium Ljungdahlii Petc Sp. Nov., A New Acetogenic, Gram–Positive, Anaerobic Bacterium, R. S. Tanner and D. Yang, Abstracts of the 1990 Annual Meeting of the American Society for Microbiology, No. R–21, p. 249.

Indirect Coal Liquification, Gaddy, Technical Report, 1985 Study of Gaseous Substrate Fermentations: Carbon Monoxide Conversion to Acetate, 2. Continuous Culture; Vega et al., Biotechnology and Bioengineering, vol. 34, pp. 785–793 (1989).

Production of Acetic Acid by *Acetogenium kiyui*: Klemps, et al., Applied Microbiology and Biotechnology, vol. 27; pp. 229–234 (1987).

Mechanism of Acetate Synthesis from $CO_2$ by *Clostridium acidiurici*Waber, et al., Journal of Bacteriology, Nov. 1979, pp. 468–478.

Biological Upgrading of Coal–derived Synthesis Gas: Final Report; Abstract; Barik et al., Fossil Fuels, vol. 110, p. 201.

Bioconversion of Synthesis Gas Into Liquid or Gases Fuels., Klasson, et al., Enzyme Microbiology Technology., 1992, vol. 14, pp. 602–608.

Biological Conversion of Coal Synthesis Gas to Methane; S Barik et al., Energy Progress, vol. 7, No. 3, Sep. 1987, pp. 157–160.

Chemical and Fuel Production by Anaerobic Bacteria, J. G. Zeikus, Annual Review Microbiology, 1980, pp. 423–464.

Acetic Acid Concentrations in the High Pressure Reactor with ERI2

CLOSTRIDIUM STAIN WHICH PRODUCES ACETIC ACID FROM WASTE GASES

BIOLOGICAL PRODUCTION OF ACETIC ACID FROM WASTE GASES

The U.S. Government has license rights in this invention pursuant to D.O.E. Cooperative Agreement No. DE-FC02-90CE40939 awarded by the U.S. Department of Energy.

CROSS-REFERENCE TO RELATED APPLICATIONS

This application is a division of application Ser. No. 07/968,857, filed Oct. 30, 1992, now abandoned.

BACKGROUND OF THE INVENTION

The present invention is directed to biological methods, processes and apparatus for producing organic acids, alcohols, and salts from the waste gas streams of certain industrial processes and more particularly concerns a process utilizing continuous gaseous substrate fermentation under anaerobic conditions to accomplish this conversion.

The conventional procedure for- producing organic acids, alcohols, and salts is chemical synthesis of petroleum-derived feedstocks. The rapidly escalating cost of petroleum has generated considerable interest in producing these valuable commodities by fermentative processes that utilize renewable or waste materials as the feedstock.

There is also growing concern over the massive amounts of atmospheric pollutants and greenhouse gases produced by conventional industrial processes. The Environmental Protection Agency recently estimated that over six million metric tons of carbon monoxide and nearly four million metric tons of hydrogen were discharged annually by the industrial complex. A substantial portion of this waste carbon monoxide and hydrogen are the result of carbon black manufacture and coke production, roughly 2.6 million metric tons of CO and 0.5 million metric tons of $H_2$. Large amounts of carbon monoxide or hydrogen are also produced by the ammonia industry (125,144 metric tons of CO in 1991), petroleum refining (8 metric tons per thousand barrels), steel mills (152 pounds per metric ton of steel produced), and sulfate pulping of wood (286 pounds per ton of pulp). In 1991, the adipic acid industry generated 40,773 metric tons of carbon monoxide that was burned for fuel value or flared. In many cases, these gases are discharged directly to the atmosphere, placing a heavy pollution burden on the environment.

Typically, the waste gases from the manufacture of industrial products are released at low pressures and temperatures. Current technology can not utilize these dilute gases under such conditions. Adapting existing technology to separate and recover hydrogen or carbon monoxide from these waste streams would be expensive and impractical.

In light of the foregoing, there is a need for a cost effective and practical method and apparatus for utilizing the above-described waste gases and for producing organic acids, alcohols and salts by other than chemical synthesis of petroleum derived feedstocks.

SUMMARY OF THE INVENTION

In accordance with the present invention, organic acids, alcohols, and/or salts are produced from the waste carbon monoxide, hydrogen, and/or carbon dioxide of industrial processes, thereby reducing environmental pollution while at the same time saving energy and chemical feedstocks.

In accordance with an exemplary process of the present invention, the desired components of the dilute gas mixtures are introduced into a bioreactor containing one or more cultured strains of anaerobic bacteria that utilize the waste gas components by a direct pathway to produce a desired organic compound. The organic compound is recovered from the aqueous phase in a separate vessel or vessels, utilizing a suitable recovery process for the compound produced. Examples of recovery processes include extraction, distillation or combinations thereof, or other efficient recovery processes. The bacteria are removed from the aqueous phase and recycled to avoid toxicity and maintain high cell concentrations, thus maximizing reaction rates. Cell separation is accomplished by centrifugation, membranous ultrafiltration, or other techniques.

Although not limited thereto, the methods and apparatus of the present invention are especially adapted to the production of acetic acid and ethanol from a waste gas stream of identical composition to that found in the manufacture of carbon black.

The principal object of the present invention is the provision of a process for the production of organic acids, alcohols, and/or salts from carbon monoxide, hydrogen, and/or carbon dioxide.

Another object of the present invention is the provision of methods and apparatus for the production of organic acids, alcohols, and/or salts from the waste gas streams of industrial processes such as oil refining, carbon black, coke, ammonia, and methanol production.

A still further object of the present invention is the provision of a process for producing acetic acid and ethanol from a waste gas stream of identical composition to that found in the manufacture of carbon black.

Yet another and more particular object of the present invention is the provision of a method and apparatus involving continuous gaseous substrate fermentation under anaerobic conditions to accomplish the conversion of waste gas streams of certain industrial processes into useful products such as organic acids, alcohols, and salts.

Other objects and further scope of the applicability of the present invention will become apparent from the detailed description to follow, taken into conjunction with the accompanying drawings wherein like parts are designated by like reference numerals.

DETAILED DESCRIPTION OF THE PREFERRED EMBODIMENTS

The term "waste gas" or "waste gas stream" as used herein means carbon monoxide and hydrogen mixed with other elements or compounds, including carbon dioxide, in a gaseous state and which are typically released or exhausted to the atmosphere either directly or through combustion. Normally, release takes place under standard smokestack temperatures and pressures. Accordingly, the processes of the present invention are suitable for converting these atmospheric pollutants into useful products such as organic acids, alcohols and salts. These products include, but are not limited to acetic, propionic, and butyric acids, methanol, ethanol, propanol, and n-butanol, plus salts, such as calcium magnesium acetate.

Anaerobic bacteria which convert carbon monoxide and water or hydrogen and carbon dioxide into alcohols and acids include *Acetobacterium kivui, A. woodii, Butyribacterium methylotrophicum, Clostridium aceticum, C. acetobutylicum, C. formicoaceticum, C. kluyveri, C. thermoaceticum, C. thermocellum, C. thermohydrosulfuricum, C. thermosaccharolyticum, Eubacterium limosum*, and *Peptostreptococcus productus*. In the development of the present invention, new strains of anaerobic bacteria have been isolated which enact this conversion with high efficiency. Depending on the specific microorganism(s) utilized, variables which must be considered include nutrient levels in the nutrient medium, pressure, temperature, gas flow rate, liquid flow rate, reaction pH, agitation rate (if utilizing a Continuously Stirred Reactor), inoculum level, maximum substrate (introduced gas) concentrations to avoid inhibition, and maximum product concentrations to avoid inhibition.

Figure 1:
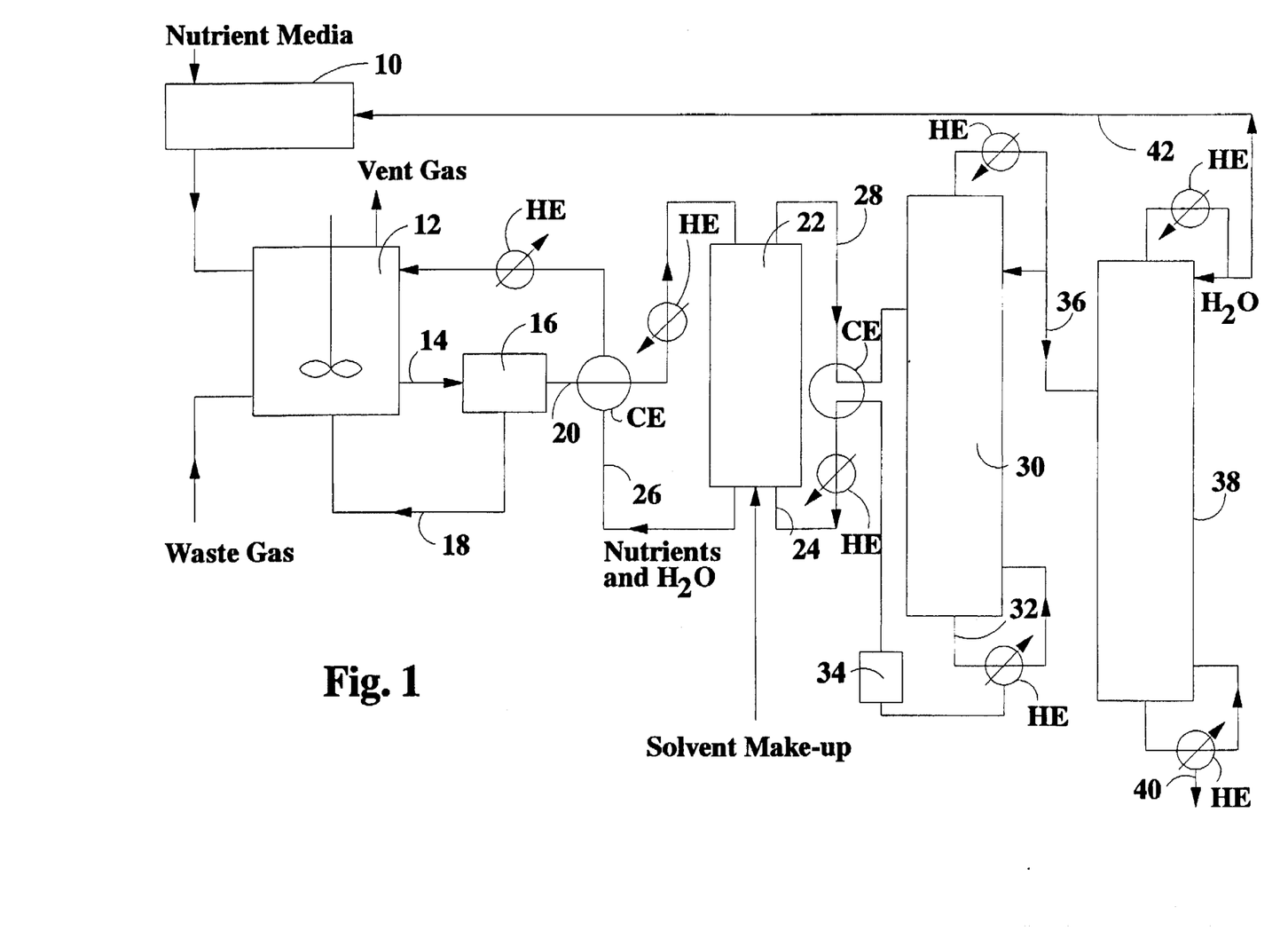
FIG. 1 is a schematic diagram of the method and apparatus in accordance with an exemplary embodiment of the present invention.

In accordance with an exemplary embodiment of the present invention and as shown in FIG. 1 of the drawings, a first step in the conversion process is the utilization of a mixing tank 10 to prepare the nutrient media for the anaerobic bacteria. The content of the nutrient media will vary based on the type of anaerobe utilized. The nutrients are constantly fed to a bioreactor 12 (fermenter), consisting of one or more vessels and/or towers of a type which includes the Continuously Stirred (CSTR), Immobilized Cell (ICR), Trickle Bed (TBR), Bubble Column, Air Lift Fermentors, or other suitable fermentation reactor. Within the bioreactor 12 resides the culture, either single or mixed species, of anaerobic bacteria utilized in the gas conversion process. For the CSTRs, these bacteria live dispersed throughout the media, but for ICRs, the bacteria adhere to an internal packing medium. This packing medium must provide maximal surface area, high mass transfer rate, low pressure drop, even gas and liquid distribution, and must minimize plugging, fouling, nesting and wall channeling. Examples of such medium materials are ceramic berl saddles or other high performance packings.

Next, the waste gases are introduced into the bioreactor. The gas is retained in the bioreactor for the period of time which maximizes efficiency of the process. Exhaust gases, if any, are then released. The liquid effluent 14 is passed to a centrifuge, hollow fiber membrane, or other filtration device 16 to separate out microorganisms that are entrained. These microorganisms 18 are returned to the bioreactor to maintain a high cell concentration which yields a faster reaction rate.

A next step in the process is separation of the desired biologically produced product(s) from the permeate or centrifugate 20. For example, the permeate or centrifugate 20 is passed to an extraction chamber 22 where it is contacted with a solvent 24. The solvent 24 should have a high distribution coefficient for the desired end product, a high recovery factor, low toxicity to humans, low toxicity to the bacteria, immiscibility with water, appropriately high boiling point, and form no emulsion with the bioreactor constituents. The distribution of solute between solvent and aqueous phase will determine the thermodynamic feasibility and the amount of solvent required to remove the end product. Typical solvents include tributyl phosphate, ethyl acetate, tri-octyl phosphine oxide, long chain alcohols, hexane, cyclohexane, chloroform, and tetrachloroethylene.

The nutrients and materials in the aqueous phase 26 pass back to the bioreactor and the solvent/acid/water or solvent/alcohol/water solution 28 passes to a distillation column 30, where it is heated to a sufficient temperature to separate the solvent from the alcohol or acid and water. The solvent 32 passes from the distillation column through a cooling chamber 34 to lower the temperature to the optimum temperature for extraction, then back to the extraction chamber 22 for reuse. The alcohol or acid and water solution 36 passes to a final distillation column 38 where the desired end product 40 is separated from the water and removed. The water 42 is recirculated to the mixing tank for nutrient preparation.

With reference again to FIG. 1, the system includes a plurality of conventional heat exchangers HE in the form of condensers (arrow pointing downwardly) and reboilers (arrow pointing upwardly). Also, cross exchangers CE are located at the junctures of lines 20 and 26 and lines 24 and 28.

Thus in accordance with the present invention it is now possible to produce valuable organic acids, alcohols, or salts by a gaseous substrate fermentation, not only reducing consumption of valuable chemical feedstocks, but also removing hazardous atmospheric pollutants from the waste gas streams of many industries. Previous processes to derive these chemicals biologically were based on fermentation of sugars.

The following specific examples are submitted to illustrate but not to limit the present invention. Unless otherwise indicated, all parts and percentages in the specification and claims are based upon volume.

EXAMPLE 1

PRODUCTION OF ACETIC ACID FROM CARBON BLACK WASTE GASES

This example is directed to a process utilized to convert waste gas of a composition which matches that of the furnace exhaust of carbon black manufacture to acetic acid. The waste gas has a composition of about 13 percent carbon monoxide, 14 percent hydrogen, and 5 percent carbon dioxide, with the remaining 68 percent largely nitrogen with traces of oxygen and sulfur compounds. The waste gases are produced as the result of partial oxidation of gas or oil with insufficient air to form amorphous carbon, with about 1.2 pounds of carbon monoxide produced per pound of elemental carbon. These waste gases form a serious atmospheric contamination problem and also represent a valuable chemical feedstock resource not presently being recovered.

Microbiology of Acetic Acid Production

Bioconversion of the gases $H_2$, $CO$, and $CO_2$, by anaerobic bacteria has been known and has been demonstrated in accordance with the present invention as having economic potential (Barik et al., 1985, 1986; 1987; Vega et al., 1988; 1989a; Clausen and Gaddy, 1985; Klasson et al., 1990; Gaddy and Clausen, 1987). Several bacterial species are capable of converting these gases into acetate, which is an intermediate product in many biological pathways.

Bacterial species such as *Acetogenium kivui* (Leigh et al., 1981), *Peptostreptococcus productus* (Barik et al., 1986; Lorowitz and Bryant, 1984), *Acetobacterium woodii* (Kerby et al., 1983), *Clostridium thermoaceticum* (Wood et al., 1982, Kerby and Zeikus, 1983), and *Eubacterium limosum* (Genthner and Bryant, 1982) produce acetate by the reaction:

$$4CO + 2H_2O \rightarrow CH_3COOH + 2CO_2 \quad dG = -39 \text{ kcal/reac.} \quad (1)$$

Many anaerobic bacteria are also known to produce acetic acid from $H_2$ and $CO_2$ (Mayer et al., 1977; Sleat et al., 1983; 1985; Balch et al., 1977). These Bacterial isolates include *A. kivui*, *P. productus*, and *Acetobacterium sp.* (Balch et al., 1977), which utilize homoacetic fermentation by anaerobically oxidizing hydrogen and $CO_2$ according to the equation:

$$4H_2 + 2CO_2 \rightarrow CH_3COOH + 2H_2O \quad dG = -25 \text{ kJ/reac.} \quad (2)$$

*Acetobacterium woodii* (Mayer et al., 1977) and *Acetoanaerobium noterae* produce acetate from $H_2$ and $CO_2$ according to the above reaction, but in addition to acetate, *A. noterae* produces some propionate and butyrate. Another chemolithotrophic bacteria, *Clostridium aceticum*, produces acetate from $CO_2$ using a glycine decarboxylase pathway (Waber and Wood, 1979).

Some bacteria, like *A. kivui*, *P. productus*, and *A. woodii*, produce acetate from either CO and $H_2O$ or $H_2$ and $CO_2$ (Vega et al., 1989; Barik et el., 1986). *P. productus* gives particularly fast rates of conversion and demonstrates high tolerance to CO; however, this organism shows a preference to follow Equation (1) over Equation (2).

In addition to these listed bacteria, two strains of an additional Clostridia which produce acetic acid or ethanol from CO and $H_2O$ or $H_2$ and $CO_2$ have been isolated. One is a *Clostridium ljungdahlii* ERI2 rod-shaped, gram positive, non-thermophilic anaerobe which gives superior acetic acid yields and operates at a low pH, which greatly enhances the recovery of the product. *C. ljungdahlii* ERI2 carries out a vigorous acetogenic fermentation of glucose. It also infrequently forms spores and carries out a primarily acetogenic fermentation of hexose or $H_2:CO_2$. It is motile with peritrichous flagellation. This new strain of *C. ljungdahlii*, referred to as ERI2, was isolated from a natural water source and was deposited on or about Dec. 8, 1992 with the American Type Culture Collection (ATCC), Rockville, Md., 12301 Parklawn Drive, Md. 20852 U.S.A. accession no. 55380. The other, *C. ljungdahlii* PETC, is described in allowed U.S. patent application Ser. No. 07/612,221 filed on Nov. 9, 1990 and is deposited with the American Type Culture Collection (ATCC), Rockville, Md., accession no. 49587.

In the development of the present process, two distinct routes to produce acetic acid from carbon black waste gases were studied. The direct route converts CO and $H_2O$ or $H_2$ and $CO_2$ directly into acetic acid according to Equations (1) and (2), respectively. An indirect route involves the conversion of CO and $H_2O$ into and $CO_2$ by the water gas shift reaction, followed by production of acetic acid from $H_2$ and $CO_2$. This indirect route was found to be a less efficient utilization of the technology.

The acetogens tested are summarized in Table 1. Among these bacteria that produce acetic acid directly from CO, *A. kivui* and the newly isolated strain, *C. ljungdahlii* ERI2, show far superior rates for both CO and $H_2$ utilization. Further experimentation proceeded using these two anaerobic bacteria.

There are obvious advantages to the bacteria utilizing carbon monoxide and hydrogen simultaneously. This would afford the most efficient use of the waste gases and remove the greatest amount of atmospheric pollutants.

Bench Scale Operation of the Described Process to Produce Acetic Acid

Figure 2:
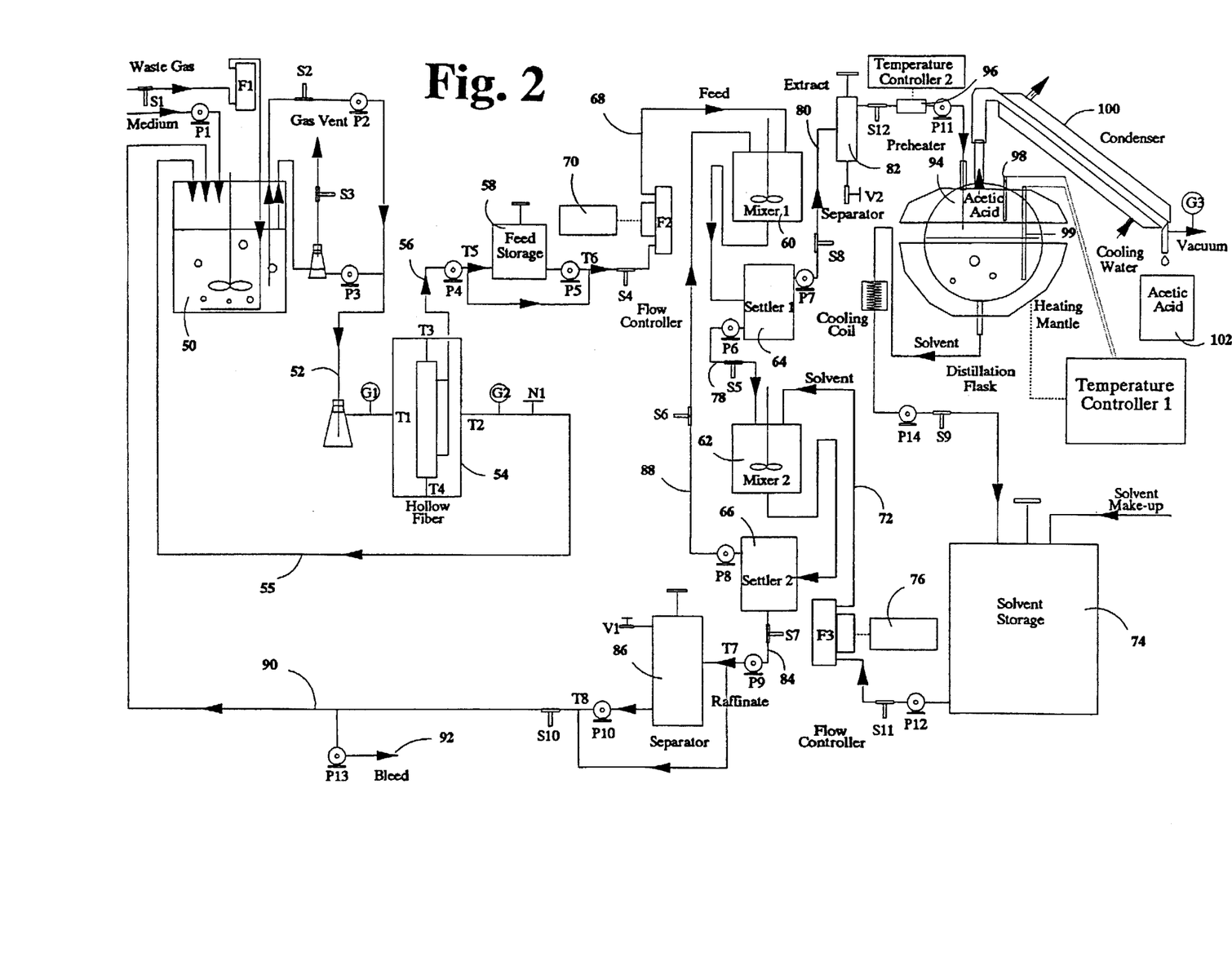
FIG. 2 is a schematic representation of a continuous fermentation system in accordance with one embodiment of the present invention.

As shown in FIG. 2 of the drawings and in accordance with one embodiment of the present invention, a bench scale continuous conversion system is shown to include a BioFlo IIC fermentor 50 from New Brunswick Scientific Co., Inc., Edison, N.J. The fermentor 50 is equipped with an agitation motor, pH controller, foam controller, thermostat, dissolved oxygen probe, nutrient pump, and 2.5 L culture vessel. The working volume is variable (1.5–2.0L). Other variable operational parameters include medium feeding rate (Dilution rate), gas flow rate (Gas retention time), agitation (rpm). The vented or exhaust gases exit the fermentor 50 through a condenser fixed to a vented hood via a water trap and a sampling port.

The culture broth 52 is recycled through a cross-flow hollow fiber module 54 by a peristaltic pump (from Cole Parmer). The recycling rate is about 80–100 mL/min. The hollow fiber module 54 has the following characteristics; the surface area is 0.35 $ft^2$, the pore size is 0.2 u and the lumen diameter is 1 mm. The permeate 56 is pumped to a storage tank 58 (Feed storage). The culture cells are returned to the fermenter along line 55.

A counter-current acetic acid extraction system, including two stage mixer and settler components includes first and second mixers 60 and 62 and first and second settling tanks 64 and 66. The permeate 68 from storage 58 is pumped to mixer 60 through a flow controller 70. The solvent 72 is pumped to mixer 62 from solvent storage 74 through a flow controller 76. Both mixer 60 and mixer 62 are equipped with a stirring mechanism to achieve good mixing of aqueous phase and solvent phase. The mixture of both phases from the mixers 60 and 62 is led to settlers 64 and 66, respectively. The phase separation is accomplished in the settlers. The aqueous phase 78 from settler 64 is pumped to mixer 62, the solvent phase 80 from settler 64 is pumped to a separator 82, the aqueous phase 84 from settler 66 is pumped to raffinate storage 86, and the solvent phase 88 from settler 66 is pumped to mixer 60. The raffinate is recycled to the CSTR 50 along a line 90. This recycle line 90 is partially bled at 92 to remove inhibiting factors.

The solvent 80 loaded with acetic acid is pumped to a distillation flask 94 through a preheater 96. The distillation flask 94 is equipped with two thermocouples 98 and 99 to monitor and control temperature in the liquid phase and gas phase. The heating temperature for distillation is set to achieve maximum vaporization of the acetic acid. The acetic acid vapors are condensed in a conderser 100 and collected in a flask 102. The stripped solvent 104 is pumped through a cooling coil 106 to solvent storage 74. With reference again to FIG. 2, the system includes conventional pumps P1–P14, sample ports S1–S12, T-intersections T1–T8, pressure gauges G1–G3, flow meters F1–F3, and valves V1, V2, and N1.

A bench scale operation of the described process as diagrammed in FIG. 2 was fabricated in the laboratory to determine quantitative yields under optimized conditions. The nutrient mixture fed to the culture was as follows:

1. 80.0 ml of a salt, composed of

| | |
|---|---|
| $KH_2PO_4$ | 3.00 g/L |
| $K2HPO_4$ | 3.00 g/L |
| (NH4)2SO4 | 6.00 g/L |
| NaCl | 6.00 g/L |
| $MgSO_4.2H_2O$ | 1.25 g/L |

2. 1.0 g of yeast extract
3. 1.0 g of trypticase 4. 3.0 ml of PFN (Pfenning) trace metal solution

| | |
|---|---|
| FeCl$_2$ * 4H$_2$O | 1500 mg |
| ZnSO$_4$ * 7H$_2$O | 100 mg |
| MnCL$_2$ * 4H$_2$O | 30 mg |
| H$_3$BO$_3$ | 300 mg |
| CoCl$_2$ * 6H$_2$O | 200 mg |
| CuCl$_2$ * H$_2$O | 10 mg |
| NiCl$_2$ * 6H$_2$O | 20 mg |
| NaMoO$_4$ * 2H$_2$O | 30 mg |
| Na$_2$SeO$_3$ | 10 mg |
| Distilled water | 1000 ml |

5. 10.0 ml of B vitamins

| | |
|---|---|
| Pyridoxal HCl | 10 mg |
| Riboflavin | 50 mg |
| Thiamine HCl | 50 mg |
| Nictotinic acid | 50 mg |
| Ca-D-Pantotheinate | 50 mg |
| Lipoic acid | 60 mg |
| P-aminobenzoic acid | 50 mg |
| Folic acid | 20 mg |
| Biotin | 20 mg |
| Cyanocobalamin | 50 mg |
| Distilled water | 1000 ml |

6. 0.5 g of Cysteine HCL
7. 0.06 g of CaCl2.2H$_2$O
8. 2.0 g of NaHCO$_3$
9. 1.0 ml of Resazurin (0.01%)
10. 920.0 ml of distilled water For use with *A kivui*, the nutrient solution was pH adjusted to 6.6, whereas for the new strain, *C. ljungdahlii* ERI2, the pH was adjusted to 4.9. As will be pointed out, the ability to operate at a lower pH is a great advantage in acetic acid recovery. The solution was then sparged for 20 minutes with a 20% CO$_2$ and 80% N$_2$ atmosphere, then transferred anaerobically and autoclaved for 15 minutes.

Numerous experiments were carried out with both Continuous Stirred Reactors (CSTR) and Immobilized Cell Reactors (ICR). The results obtained are exemplified in the following data.

CSTR Experiments Utilizing the Bacterial Strains *A. kivui* and *C. ljungdahlii* ERI2

The bench scale system operating with the CSTR and the anaerobic bacteria, *C. ljungdahlii* ERI2 and *A. kivui*, consisted of a New Brunswick Scientific Bioflow IIc fermenter, a hollow fiber membrane unit for cell recycle, and extraction and distillation columns. Nutrient mixture was fed into the bioreactor at a rate of 3.2 cubic centimeters per minute. Capacity of the reactor was 2.5 liters, within which a constant fluid level of 1.5 liters was maintained. The fluid was agitated at variable rates of up to 1000 revolutions per minute with gas introduced at a rate of approximately 500 cubic centimeters per minute. Optimal gas retention times were in the range of three minutes. The gas feed varied with its uptake by the bacteria, which was in turn a function of the cell density.

The liquid from the bioreactor was passed to the hollow fiber membrane at a rate of 55 to 70 milliliters per minute. From the hollow fiber membrane, permeate was gathered at a rate of 1.5 milliliters per minute. Analysis of this permeate indicates the acetic acid/acetate concentration at this stage to range in excess of 20 grams per liter. Operating at a pH of 4.9, 42 percent of this product was in the acid form using *C. ljungdahlii* ERI2. For *A. kivui*, the acid yield was only 1.4 percent. Results of various runs for the two bacteria, including conversion rates and product yields are summarized in Tables 2 and 3.

ICR Experiments Utilizing the Bacterial Strain *C. ljungdahlii* ERI2

An Immobilized Cell Reactor (ICR), consisting of a 2 inch outside diameter by 24 inch tall glass tube packed with fabric to support the cells and Enkamat 7020 as an immobilizing medium was also tested in the acetic acid production process. With *C. ljungdahlii* ERI2 as the acetogenic anaerobe, 100 percent of the carbon monoxide and 79 percent of the hydrogen were converted at a gas retention time of 20 minutes. Acetic acid concentrations in the removed liquid were approximately 6.0 grams per liter. Results of the ICR studies are summarized in Table 4.

The ICR has a certain attractiveness on an industrial scale in that the energy costs to operate the reactor are reduced significantly. The proper selection of packing materials, solution phases, and pressures may yield production approaching that of the CSTR.

Acetic Acid Recovery

Various solvents were tested for recovering acetic acid from the permeate, the results are summarized in Table 5. Tributyl phosphate was identified as having both a high distribution coefficient and a high boiling point. The solvent and permeate from the cell separator were commingled in a two stage extraction process. Alternatively, an extraction column could be used. Permeate was introduced into a 3 liter flask where it was mixed with incoming solvent. A ratio of 1 part solvent to 1 part permeate worked well and gave high recovery rates. The combined fluids were passed from the mixer to a 4 liter settling chamber where the solvent/acetic acid mixture separate as a lower density phase from the water and nutrients. Retention times of approximately 15 minutes were used in the settling tanks. The lower density phase was extracted and fed to a distillation flask. The raffinate was passed from the first settler to a second mixer where it was contacted again with solvent, then removed to a second settling chamber. This allowed for more complete extraction of the acetic acid; acid recovery increased from 82 percent to greater than 96 percent using tributyl phosphate. The solvent/acetic acid mixture from this settler was returned to the first mixer, while the raffinate of water and organics was passed back to the bioreactor.

The distillation unit was a 5 liter flask with a boiling mantle. A common distillation column, with reflux, could be used for complete acid recovery. Because of the high boiling point of tributyl phosphate, nearly complete recovery is accomplished in one step. The solvent/acetic acid mixture was heated to 120 degrees C., with the acetic acid collected overhead in a condensing coil. In this single stage system, distillation efficiencies of 70 percent were achieved.

Solvent mixtures were also tried and distribution coefficients of mixed solvents are summarized in Table 6.

EXAMPLE 2

PRODUCTION OF ETHANOL FROM CARBON BLACK WASTE GASES

Microbiology of Ethanol Production

Bioconversion of carbon monoxide, hydrogen, and carbon dioxide to ethanol has received relatively little study, hence not many organisms which carry out this reaction are known. This is in part a result of the preference of most anaerobic microorganisms utilizing the necessary pathway to produce acetate. At the present time, only *C. ljungdahlii* PETC (ATCC No. 49587) and ERI2 (ATCC No. 55380) are known to produce ethanol in significant amounts from gaseous substrates containing carbon monoxide. This reaction takes place according to the following stoichiometry:

$$6CO + 3H_2O \rightarrow CH_3CH_2OH + 4CO_2 \quad (3)$$

$$2CO_2 + 6H_2 \rightarrow CH_3CH_2OH + 3H_2O \quad (4)$$

Bench Scale Process to Produce Ethanol

The bench scale process to produce ethanol was essentially the same as that for producing acetic acid. Ethanol production takes place at the expense of acetic acid production in this system. Variables which enhance ethanol yield include: nutrient limiting the culture; adding biotin and thiamine to the culture; lowering pH and dilution rates; and using reducing agents, such as cysteine hydrochloride or benzyl viologen in low concentrations. Productivity is maximized by assuring that adequate amounts of gaseous substrate are available to the culture (ethanol is consumed when the gas is limited) and by maintaining high agitation rates when using the CSTR. Continuous product recovery, using extractive fermentation is also essential to prevent conversion of ethanol to acetate.

Operating with a fed batch unit, *C. ljungdahlii* ERI2 performed as follows:

pH: 4.5
Agitation Rate: 1000 RPM
Gas Flow Rate: 20 ml/min
CO Conversion Rate: 65–75%
Ethanol Production: 9.7 g/L
Acetic Acid Production: 2.0 g/L

EXAMPLE 3

PRODUCTION OF ACETIC ACID FROM CARBON BLACK WASTE GASES AT HIGHER PRESSURES

Figure 3:
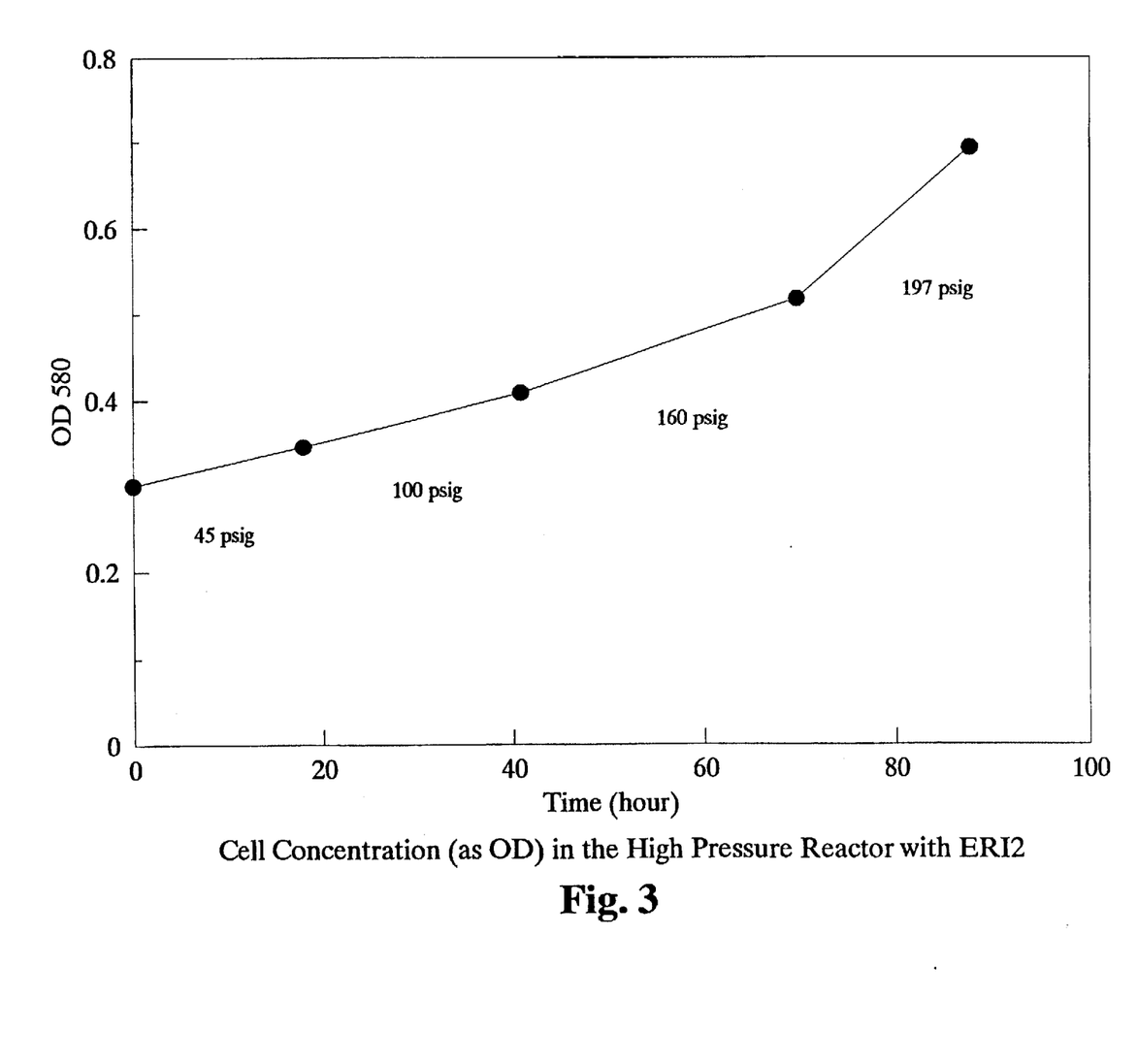
FIG. 3 is a graphical illustration of cell concentration (OD) versus time.
Figure 4:
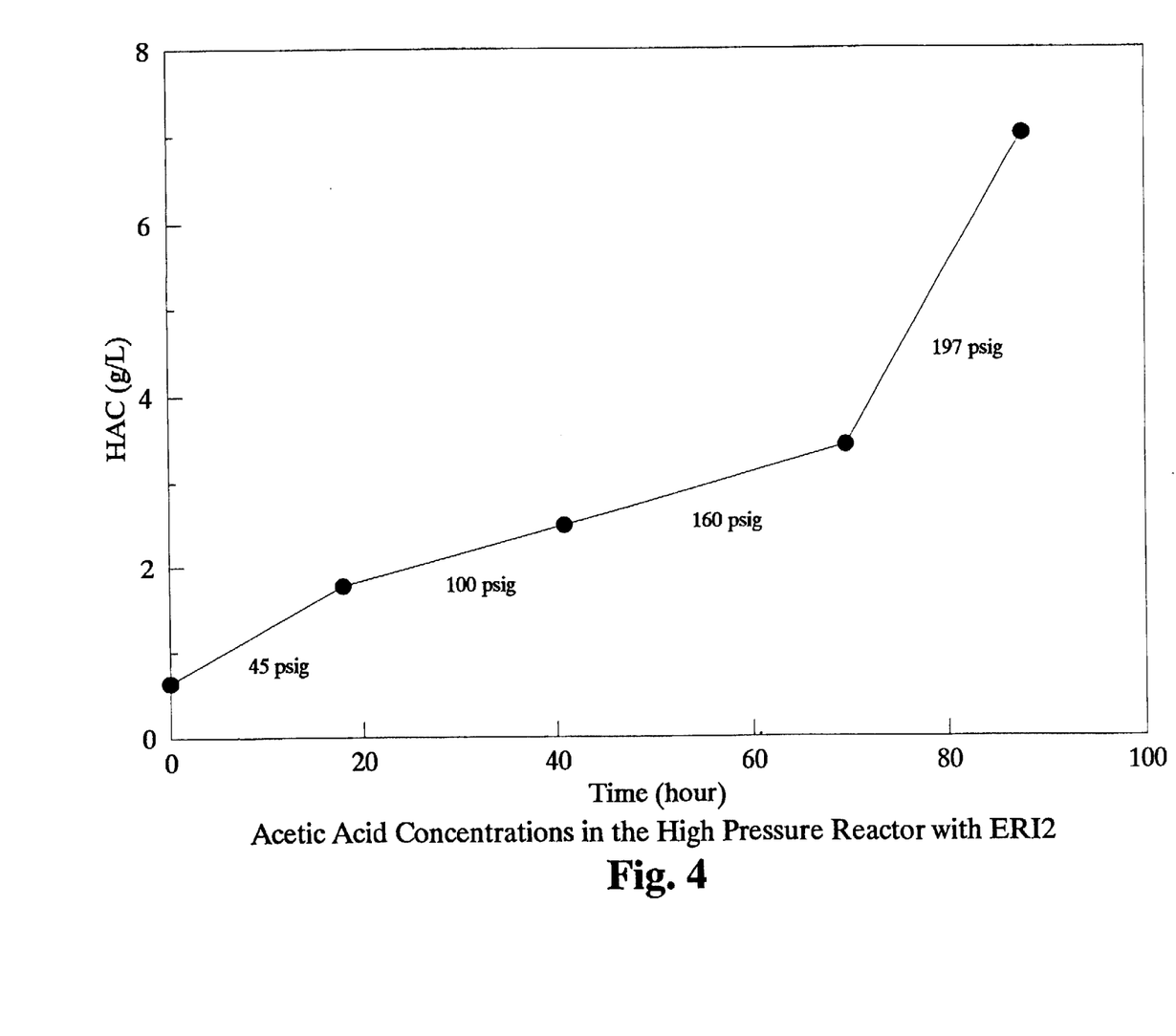
FIG. 4 is a graphical representation of acetic acid concentration (HAC) versus time.

Mass transport in the cellular reactions can be further enhanced by operating the system at increased pressures. Simple batch experiments were carried out to test the dynamics of this system. It was found that reaction rates increased in linear proportion to the pressure, with a corresponding reduction in effective retention time. Another advantage to operating at increased pressure is that reactor volume can also be reduced in linear fashion, i.e. operation at 10 atmospheres pressure requires a reactor with one tenth the volume of a reactor operating at 1 atmosphere. FIGS. 2 and 3 show the increase in cell density and acetic acid concentration, respectively, with the increased pressure. This acetic acid concentration far exceeds typical batch concentrations for a batch reactor at atmospheric pressure.

EXAMPLE 4

PRODUCTION OF ACETIC ACID FROM CARBON BLACK WASTE GASES WITH SURFACTANTS

Mass transport is also increased by the use of surfactants. Table 7 presents the results of carbon monoxide uptake tests performed on *C. ljungdahlii* ERI2 in the presence of various commercial surfactants. In each case, the control value of 100 (percent) represents CO uptake in batch fermentation, and the sample value, the percentage of the control in batch fermentation in the presence of the surfactant.

In accordance with one embodiment, the present invention is directed to a process for producing organic acids, alcohols, or salts from a waste gas stream, including the steps of: fermenting the waste gas anaerobically with at least one microorganism in a bioreactor to produce an organic acid, alcohol, or salt product, continuously removing a product containing broth from the bioreactor, and recovering the product acid, alcohol, or salt from the broth of the bioreactor. The waste gas is generated by industrial processes such as carbon black, ammonia, or methanol production, petroleum refining, or coke manufacture and contains carbon monoxide and water and/or carbon dioxide and hydrogen. The microorganism is of a species which produce organic acids or alcohols by anaerobic fermentation of gaseous substrates. The products are selected from the group including acetic acid, propionic acid, butyric acid, methanol, ethanol, propanol, N-butanol, and salts, such as calcium magnesium acetate.

Thus it will be appreciated that as a result of the present invention, a highly effective improved process for converting waste gases to organic acids or alcohols is provided by which the principal objective, among others, is completely fulfilled. It is contemplated, and will be apparent to those skilled in the art from the preceding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

TABLE 1

ACETOGENIC BACTERIA TESTED FOR CO, $H_2$, AND $CO_2$ CONVERSION

| Bacterial Route | Simultaneous Consumption of CO and $H_2$ |
|---|---|
| Direct Route | |
| P. productus | No |
| E. limosum | No |
| A. noterae | No |
| C. aceticum | No |
| C. thermoaceticum | No |
| S. sphaeroides | No |
| A. woodii | Yes |
| A. kivui | Yes |
| C. ljungdahlii ERI2 | Yes |
| Indirect Route | |
| R. rubrum (ATCC 9791) | No |
| R. rubrum (ATCC 25903) | No |
| R. gelatinosa | No |

TABLE 2

Summary of ERI2 Experiments in the CSTR with Cell Recycle

| Gas Reten. Time (min) | Liquid Dilution Rate (hr⁻¹) | Agitat. Rate (rpm) | Percent Gas Conversion CO | Percent Gas Conversion H₂ | Dry Cell Weight Conc. (g/L) | Product Concentration HAC (g/L) | Product Concentration ETOH (g/L) | Specific Productivities (g/L hr) | Specific Productivities (g/g hr) |
|---|---|---|---|---|---|---|---|---|---|
| 9.30 | 0.056 | 750 | 80.75 | 74.5 | 2.3 | 9.7 | 0.07 | 0.43 | 0.18 |
| 9.28 | 0.055 | 750 | 82.1 | 72.0 | 3.32 | 9.56 | 0.094 | 0.52 | 0.16 |
| 6.14 | 0.061 | 750 | 73.6 | 46.5 | 4.11 | 12.78 | 0.125 | 0.78 | 0.19 |
| 6.4 | 0.08 | 750 | 74.8 | 49.6 | 5.02 | 12.98 | 0.125 | 1.05 | 0.19 |
| 4.74 | 0.087 | 750 | 68.5 | 37.2 | 4.79 | 12.38 | 0.125 | 1.08 | 0.23 |
| 4.91 | 0.10 | 750 | 68.8 | 50.2 | 4.53 | 10.73 | 0.05 | 1.08 | 0.24 |
| 4.05 | 0.102 | 750 | 65.5 | 58.1 | 5.27 | 11.49 | 0.076 | 1.17 | 0.22 |
| 3.98 | 0.103 | 900 | 74.3 | 67.9 | 6.17 | 12.73 | 0.1 | 1.31 | 0.21 |
| 2.89 | 0.117 | 900 | 66.1 | 33.9 | 5.91 | 11.69 | 0.04 | 1.38 | 0.23 |
| 3.28 | 0.105 | 1000 | 74.6 | 51.3 | 7.30 | 12.83 | 0.13 | 1.35 | 0.18 |
| 3.22 | 0.125 | 1000 | 73.1 | 54.0 | 10.25 | 13.57 | 0.08 | 1.71 | 0.17 |
| 2.65 | 0.13 | 1000 | 68.9 | 44.0 | 11.0 | 14.63 | 0.12 | 1.90 | 0.17 |
| 2.3 | 0.134 | 1000 | 66.0 | 38.7 | 11.1 | 20.59 | 0.113 | 2.77 | 0.25 |
| 2.7 | 0.11 | 1000 | 72.7 | 67.7 | 8.37 | 25.62 | 0.27 | 2.88 | 0.34 |
| 2.4 | 0.11 | 1000 | 68.6 | 63.3 | 9.88 | 26.82 | 0.36 | 2.95 | 0.30 |
| 2.55 | 0.122 | 1000 | 72.1 | 67.4 | 9.82 | 25.62 | 0.72 | 3.12 | 0.32 |
| 3.0 | 0.13 | 1000 | 76.6 | 73.3 | 12.4 | 22.33 | 0.52 | 2.90 | 0.23 |

TABLE 3

Summary of A. kivui Experiments in the CSTR with Cell Recycle

| Gas Reten. Time (min) | Liquid Dilution Rate (hr⁻¹) | Agitat. Rate (rpm) | Percent Gas Conversion CO | Percent Gas Conversion H₂ | Dry Cell Weight Conc. (g/L) | Product Concen. (g/L) | Specific Productivities (g/L hr) | Specific Productivities (g/g hr) |
|---|---|---|---|---|---|---|---|---|
| 5.0 | 0.058 | 750 | 67.8 | 44.2 | 4.00 | 16.15 | 0.96 | 0.24 |
| 4.4 | 0.958 | 750 | 65.7 | 38.5 | 4.8 | 16.63 | 0.94 | 0.19 |
| 4.3 | 0.058 | 900 | 71.3 | 40.7 | 4.5 | 17.03 | 0.99 | 0.21 |
| 3.72 | 0.058 | 900 | 69.0 | 37.3 | 5.14 | 19.16 | 1.13 | 0.22 |
| 3.72 | 0.076 | 900 | 70.3 | 41.1 | 5.28 | 16.17 | 1.21 | 0.23 |
| 3.2 | 0.076 | 900 | 66.4 | 41.4 | 5.71 | 16.85 | 1.23 | 0.23 |
| 2.8 | 0.076 | 900 | 61.5 | 29.1 | 5.00 | 16.16 | 1.22 | 0.23 |
| 2.8 | 0.076 | 1000 | 69.5 | 36.3 | 5.8 | 18.58 | 1.62 | 0.29 |
| 2.8 | 0.11 | 1000 | 70.2 | 41.6 | 5.9 | 18.4 | 1.84 | 0.36 |
| 2.2 | 0.11 | 1000 | 64.0 | 28.0 | 7.2 | 16.5 | 2.1 | 0.3 |

TABLE 4

Fabric ICR Performance with ERI2

| Liquid Dilution Rate (hr) | Gas Retention Time (min) | H₂ Conversion (%) | CO Conversion (%) | Cell Concen. (g/L) | Product Concentration HAC (g/L) | Product Concentration ETOH (g/L) |
|---|---|---|---|---|---|---|
| 0.23 | 4.83 | 38.62 | 54.66 | .125 | 3.221 | .778 |
|  | 7.41 | 49.15 | 70.87 | .120 | 2.690 | .620 |
|  | 11.66 | 51.31 | 80.61 | .067 |  |  |
|  | 13.61 | 56.87 | 83.93 | .064 | 2.099 | .201 |
| 0.17 | 6.39 | 48.15 | 73.27 | .161 | 3.382 | 1.366 |
|  | 11.21 | 68.96 | 92.82 | .143 | 3.189 | .495 |
|  | 55.44 | 83.13 | 98.27 | .112 | .813 | .058 |
| 0.12 | 6.26 | 43.89 | 70.76 | 0.94 | 3.864 | 1.689 |
| 0.09 | 7.87 | 42.40 | 79.72 | .095 | 4.423 | 2.733 |
|  | 19.82 | 59.63 | 92.92 | .102 |  |  |
| 0.03 | 22.14 | 55.01 | 94.21 | .071 | 4.878 | 2.631 |
|  | 29.00 | 78.60 | 100 | .018 | 5.604 | 2.748 |
|  | 60.48 | 83.33 | 100 |  |  |  |

TABLE 5

Acetic Acid Distribution Coefficient Study

| Solvent | Equilibrium Aqueous Acetic Acid Concentration, g/L | Acetic Acid Distribution Coefficients |
|---|---|---|
| Hexane | 6.559 | 0.0 |
| Decane | 5.968 | 0.08 |
| Chloroform | 5.128 | 0.09 |
| Kerosene | 4.648 | 0.11 |
| Hexadecane | 5.866 | 0.13 |
| Dodecane | 4.654 | 0.13 |
| Dodecyl acetate | 5.787 | 0.15 |
| Dibutyl phosphate | 4.615 | 0.18 |
| Oleyl alcohol | 5.114 | 0.28 |
| Trioctylamine | 3.785 | 0.31 |
| Undecyl alcohol | 4.528 | 0.40 |
| Ethyl acetate | 4.550 | 0.41 |
| Ethyl butyrate | 4.665 | 0.42 |
| Dexyl alcohol | 3.890 | 0.42 |
| Octanol | 4.358 | 0.45 |
| Nonyl alcohol | 3.470 | 0.55 |
| 2-ethyl-1-hexanol | 3.308 | 0.77 |
| 3-methylcyclohexanol | 2.110 | 1.26 |

TABLE 5-continued

Acetic Acid Distribution Coefficient Study

| Solvent | Equilibrium Aqueous Acetic Acid Concentration, g/L | Acetic Acid Distribution Coefficients |
|---|---|---|
| Cyclohexanone | 2.702 | 1.66 |
| Tributyl Phosphate | 1.657 | 2.38 |

TABLE 6

Distribution Coefficients of Mixed Solvents

| Solvent Mix | Distribution Coefficients | Percent Increase |
|---|---|---|
| Oleyl Alcohol (10 cc) | 0.17 | |
| Oleyl Alcohol (10 cc) + Cyc (1 cc) | 0.31 | 72 |
| Oleyl Alcohol (10 cc) + TBP (1 cc) | 0.29 | 61 |
| Oleyl Alcohol (10 cc) + Cyc (2 cc) | 0.45 | 150 |
| Oleyl Alcohol (10 cc) + TBP (2 cc) | 0.42 | 133 |
| Oleyl Alcohol (10 cc) + Cyc (3 cc) | 0.36 | 100 |
| Oleyl Alcohol (10 cc) + TBP (3 cc) | 0.42 | 133 |
| Oleyl Alcohol (10 cc) + Cyc (4 cc) | 0.35 | 94 |
| Oleyl Alcohol (10 cc) + TBP (4 cc) | 0.40 | 122 |
| Oleyl Alcohol (10 cc) + Cyc (6 cc) | 0.52 | 188 |
| Oleyl Alcohol (10 cc) + TBP (6 cc) | 0.65 | 261 |
| Oleyl Alcohol (10 cc) + Cyc (7 cc) | 0.69 | 283 |
| Oleyl Alcohol (10 cc) + TBP (7 cc) | 0.74 | 311 |

TABLE 7

CO Consumption by ERI2 in the Presence of Surfactants

| | Control* | With Surfactant |
|---|---|---|
| DNAP (0.1%, v/v) | 100 | 0 |
| Nondiat P-40 (0.1%, v/v) | 100 | 0 |
| Tergitol NP-10 (0.1%, v/v) | 100 | 0 |
| Tergitol Min Foam 1X (0.1%, v/v) | 100 | 0 |
| Tergitol TMN-10 (0.1%, v/v) | 100 | 0 |
| Triton X-15 (0.1%, v/v) | 100 | 0 |
| Triton X-100 (0.1%, v/v) | 100 | 0 |
| Triton X-114 (0.1%, v/v) | 100 | 0 |
| Triton N-101 (0.1%, v/v) | 100 | 5.83 |
| Triton X-405 (0.1%, v/v) | 100 | 7.82 |
| Tergitol 8 (0.1%, v/v) | 100 | 12.15 |
| Triton N-42 (0.1%, v/v) | 100 | 42.90 |
| Witconol NS-500K (0.01%, w/v) | 100 | 79.08 |
| Tween 85 (0.1%, v/v) | 100 | 82.16 |
| Witconol H-33 (0.1%, v/v) | 100 | 90.12 |
| Witconol 6903 (0.1%, v/v) | 100 | 92.39 |
| Tween 80 (0.1%, v/v) | 100 | 97.15 |
| Arlacel 83 (0.1%, v/v) | 100 | 97.43 |
| Span 80 (0.1%, v/v) | 100 | 99.12 |
| Tyloxapol (0.1%, v/v) | 100 | 104.86 |
| Witconol 5906 (0.1%, v/v) | 100 | 108.42 |
| Span 85 (0.1%, v/v) | 100 | 124.85 |
| W-1 (0.01%, w/v) | | |
| First time | 100 | 105.89 |
| Second time regas | 100 | 0 |
| Brij 96 (0.004%, w/v) | | |
| First time | 100 | 107.98 |
| Second time | 100 | 0 |

LIST OF REFERENCES

Balch, W. E., S. Sohoberth, R. S. Tanner, and R. S. Wolfe: "Acetobacterium New Genus of Hydrogen-Oxidizing, Carbon-Dioxide-Reducing Anaerobic Bacteria," *Int'l. J. Syst. Bacteriology* (1977) 27: 355–361.

Barik, S., R. E. Corder, E. C. Clausen, and J. L. Caddy: "Biological Conversion of Coal Synthesis Gas to Methane," presented at the American Institute of Chemical Engineers Summer National Meeting, Seattle (August 1985).

Barik, S., G. C. Magruder, R. E. Corder, E. C. Clausen, and J. L. Caddy. "Biological Conversion of Coal Gas To Chemicals and Methane," presented at the 86th American Society of Microbiology National Meeting, Washington, D.C. (March 1986).

Barik, S., R. E. Corder, E. C. Clausen, and J, L. Caddy. *Energy Progress,* 7, p. 157 (1987).

Braun, M. S. Sohoberth, and G. Gottschalk; "Enumeration of Bacteria Forming Acetate from Hydrogen and Carbon Dioxide inAnaerobic Habitats," *Arch. Microbiol.* (1979) 120: 201–224.

Clausen, E. C. and J. L. Caddy: "Biological Conversion of Coal Synthesis Gas," Annual Report, US DCE—Morgantown Energy Technology Center, (May 1985).

Dashekvicz, M. P. and R. L. Uffen: "identification of a Carbon Monoxide Metabolizing Bacteria as a Strain of *Rhodopseudomonas gelatinosa* (molish) van Neil Int," *J. Syst. Bacteriol.* (1979) 29: 145–148.

Gaddy, J. L. and E. C. Clausan: "Biological Conversion of Coal Synthesis Gas," *Proceedings of the EPRI Workshop on Biological Coal Conversion,* (1987).

Genthner, B. R. S. and M. P. Bryant "Growth of *Eubacterium limosum* with Carbon Monoxide as the Energy Source" *Appl. Environ Microbiol.* (1982) 43: 70–74

Goodell, R. et al *Coal Outlook, p.* 3 (Jan. 9, 1984).

Hagler, Bailly and Company, "Industrial Waste Gas Streams Control Technologies and R & D Programs," Final Report Prepared for the Dewar truant of Energy (June 1986).

Kerby, R., W. Niemczura, and J. G. Zeikus. "Single Carbon Catabolism in *Acetobacterium woodii* and *Butyribacterium methylotrophicum* by Fermentation and 13C Nuclear Magnetic Resonance Measurement," J Bacteriol (1983) 155: 1208–1218.

Kathy, R. and J. G. Zeikus. "Growth of Clostridium thermoaceticum on $H_2/CO_2$ or CO as Energy Source," *Curr. Microbiol.* (1983) 8: 27–30.

Klemps, R., S. M. Schoberth, and H. Sahm. "Production of Acetic Acid by *Acecogenium kivui,"* *Appl. Microbiol. Biotechnol.,* 27, 229–234 (1987).

Klasson, K. T., M. D. Ackerson, E. C. Clausen, and J. L. Caddy: "Bioconversion of Synthesis Gas into Liquid or Gaseous Fuels," *Proceedings Int'l, Sync. on Biol. Proc. of Coal,* EPRI and DOE, Orlando, May 1990a.

Leigh, J. A., F. Mayer, and R. S. Wolfe. "*Acetogenium kivui,* a New Thermophilic Hydrogen-Oxidizing Acetogenic Bacterium," *Arch. Microbiol.,* 129, 275–280 (1981).

Lorowitz, W. H. and M. P. Bryant: "*Peptostreptococcus productus* Strain Grows Rapidly with CO as the Energy Source," *Appl. Environ. Microbiol,* (1984) 47: 961–964.

Mayer, F., R. Lurz, and S. Schoberth: "Electron Microscopic Investigation of the Hydrogen-oxidizing Acetate-forming Anaerobic Bacterium *Acetobacterium wooalii,"* *Arch. Microbiol.* (1977) 115: 207–214.

McKetta, J. *Encl. of Chem. Proc. and Design,* 9, (1976).

McKetta, J. *Chemical and Engr New,* p. 35 (Jun. 9, 1986).

Schwartz, R. and F. A. Keller, Jr. "Isolation of a Strain of *Closctidium thermoaceticum* capable of Growth and Acetic Acid Production at pH 4.5," *Appl. Environ. Microbiol.,* 43, 117–123 (1982a).

Schwartz, R. and F. A. Keller, Jr. "Acetic Acid Production by *Clostridium thermoaceticum* in pH-Controlled Batch Fermentations at Acidic pH," *Appl. Environ. Microbiol.,* 43, 1385–1392 (1982b).

Sleat, R., R. A. Mah, and R. Robinson: "Isolation and Characterization of an Anaerobic Hydrogen-Utilizing Acetate-Forming Bacterium," Proc., 83rd Annual Meeting of the American Society for Microbiology New Orleans (Mar. 6–11, 1983) 83: 154.

Uffen, R. L.: "Anaerobic Growth of a *Rhodopseudomonas Species* in the Dark with Carbon Monoxide as the Sole Carbon and Energy Substrate," Proc., Nat'l. Aced. Sci. U.S.A. (1979) 73: 3298–3502.

Uffen R. L.: "Metabolism of Carbon Monoxide by *Rhodopseudomonas gelatinosa:* Cell Growth and Properties of the Oxidation System," *J. Bacteriol.* (1983) 155: 956–965.

Vega J. L. G. M. Antorrena E. C. Clausen, and J. L. Gaddy. "Biological Production of Liquid and Gaseous Fuels from Coal Synthesis Gas," *ACS Symposium Series,* (1988).

Vega, J. L., G. M. Antorrena, E. C. Clausen and J. L. Caddy: "Study of Gaseous Substrate Fermentations: Carbon Monoxide Conversion to Acetate, 2. Continuous Culture," *Biotechnology and Bioengineering* (1989a), 34 p. 785.

Waber, L. J., and H. G. Wood: "Mechanism of Acetate Synthesis from $CO_2$ by *Clostridium acidiurici,*" *J. Bacteriol.* (1979) 140: 468–478.

Wood, H. G., H. L. Drake, and S. Hu: "Studies with *Clostridium Thermoaceticum* and the Resolution of the Pathway Used by Acetogenic Bacteria that Grow on Carbon Monoxide or Carbon Dioxide and Hydrogen," *Proc., Biochem. Symp.* (1982) pp 29–56.

Yang, H., S. L. Daniel, T. Hsu, and H. L. Drake, "Nickel Transportation by the Thermophilic Acetogen *Acetogenium kivui,*" *Appl. Environ. Microbiol.,* 55, 1078–1081 (1989).

Yang, H. and H. L. Drake, "Differential Effects of Sodium on Hydrogen- and Glucose-Dependent Growth of the Acetogenic Bacterium *Acetogenium kivui,*" *Appl. Environ. Microbiol,* 56, 81–86 (1990).

*National Air Pollutant Emission Estimates*, 1940–84, EPA-450/4-85-014 (January 1986).

What is claimed is:

1. A biologically pure culture of the microorganism *Clostridium ljungdahlii* having all of the identifying characteristics of ATCC No. 55380.

2. The biologically pure culture of claim 1 wherein the microorganism, under anaerobic conditions, has the ability to produce acetate upon fermentation in an aqueous nutrient medium containing waste gas as a substrate.

3. The biologically pure culture of claim 2 wherein said substrate is a carbon black waste gas.

4. The biologically pure culture of claim 1 wherein the microorganism, under anaerobic conditions, has the ability to convert CO and water to acetic acid.

5. The biologically pure culture of claim 1 wherein said culture, under anaerobic conditions, has the ability to convert each of $CO_2$ and $H_2$ and CO and water to acetic acid.

6. The biologically pure culture of claim 1 wherein the microorganism is able to carry out acetogenic fermentation of glucose.

7. The biologically pure culture of claim 1 wherein the microorganism has the ability to anaerobically produce acetate upon fermentation in an aqueous nutrient media containing $CO_2$ and $H_2$ gases.

* * * * *

UNITED STATES PATENT AND TRADEMARK OFFICE
Certificate

Patent No. 5,593,886                                                          Patented: January 14, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James L. Gaddy, Fayetteville, Arkansas; and Guangjiong Chen, Chesterfield, MO.

Signed and Sealed this Sixteenth Day of January 2007.

WILLIAM R. DIXON, JR.
*Special Program Examiner*
Technology Center 1600